(12) United States Patent
Alfano et al.

(10) Patent No.: US 10,433,731 B2
(45) Date of Patent: Oct. 8, 2019

(54) CONTINUOUS DIODE LASER STIMULATED RAMAN GAIN/LOSS VIBRATIONAL MICROSCOPE

(71) Applicant: Robert R. Alfano, Bronx, NY (US)

(72) Inventors: Robert R. Alfano, Bronx, NY (US);
Lingyan Shi, New York, NY (US);
Yury Budansky, Oakland, NJ (US)

(*) Notice: Subject to any disclaimer, the term of this patent is extended or adjusted under 35 U.S.C. 154(b) by 131 days.

(21) Appl. No.: 15/243,207

(22) Filed: Aug. 22, 2016

(65) Prior Publication Data

US 2017/0127947 A1   May 11, 2017

Related U.S. Application Data (60) Provisional application No. 62/283,067, filed on Aug. 20, 2015.

(51) Int. Cl.
*A61B 5/00*   (2006.01)
*G01N 21/65*   (2006.01)

(52) U.S. Cl.
CPC .......... *A61B 5/0075* (2013.01); *A61B 5/0068* (2013.01); *G01N 21/65* (2013.01); *G01N 2021/655* (2013.01); *G01N 2201/0612* (2013.01)

(58) Field of Classification Search
CPC .... A61B 5/0075; A61B 5/0068; G01N 21/65; G01N 2021/655; G01N 2201/0612
See application file for complete search history.

(56) References Cited

U.S. PATENT DOCUMENTS

| 6,560,478 | B1* | 5/2003 | Alfano | A61B 5/0075 600/473 |
| 2010/0309465 | A1* | 12/2010 | Liu | G01J 3/44 356/301 |
| 2013/0162994 | A1* | 6/2013 | Xie | G01N 21/171 356/342 |

OTHER PUBLICATIONS

A. Owyoung and E. Jones, Optics Letters 1, 152 (Nov. 1977) "Stimulated Raman spectroscopy using low-power cw lasers".

(Continued)

*Primary Examiner* — Rex R Holmes
(74) *Attorney, Agent, or Firm* — Myron Greenspan Lackenbach Siegel LLP (57) ABSTRACT

There is a need for a compact instrument and microscope that maps the vibration fingerprints of biomolecules and chemicals in a sample such as brain, breast, cervix, and arteries. One can use spontaneous Raman scattering to accomplish this; however, the problem is low scattering efficiency to $10^{-5}$. With the availability of continuous wave diode laser at numerous wavelengths from 375 nm-1800 nm for parametric nonlinear difference vibrational mixing to enhance Stimulated Raman process within materials. A seed beam at Raman frequency is used with pump laser beam. In this way one can map in 2D and 3D images of the vibrations associate with disease changes. Scanning a pair of laser beams can map the location of vibrations within cells, smears, membranes, arteries, and tissues of animal and human.

19 Claims, 7 Drawing Sheets

(56) References Cited

OTHER PUBLICATIONS

C-R Hu, Optics Letters 38, 1479 (May 2013) "Stimulated Raman scattering imaging by continuous-wave laser excitation".
B. Saar, Science, 330, 1368 (2010) "Video-rate molecular imaging in vivo with stimulated Raman scattering".
P. Nandakumar, Journal of Physics, 11, U 33026 (2009) "Vibrational imaging based on stimulated Raman scattering microscopy".
Marieke Pudles, J, Biophotonics 6,205 (2013) "Non-invasive identification of proteoglycans and chondrocyte differentiation state by Raman microspectroscopy".

* cited by examiner

CONTINUOUS DIODE LASER STIMULATED RAMAN GAIN/LOSS VIBRATIONAL MICROSCOPE

BACKGROUND OF THE INVENTION

1. Field of the Invention

The invention generally relates to Raman Microscopes and, more specifically, to continuous diode laser stimulated raman gain/loss vibrational microscopes.

2. Description of Prior Art

Figure 1:
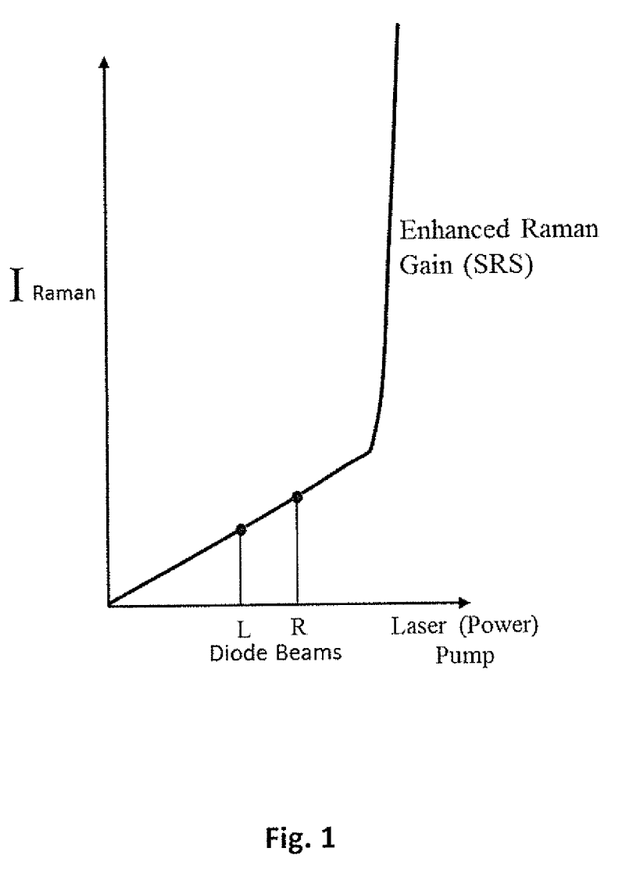
FIG. 1 shows the relationship between the intensity of Raman signal versus the pump laser power.

Raman scattering is used to measure the vibrational spectra in materials. The Raman process is weak. The Raman intensity is $\sim 10^{-6} I_L$ about 1 Raman photon is scattered for every $10^6$ laser incident photons. The intensity of Raman signal versus pump laser power is shown in FIG. 1 where spontaneous and stimulated Raman regions are indicated. Enhanced or stimulated Raman Scattering (SRS) can be used for most intensity peaks and narrowest Raman vibration lines. In SRS, the Raman beam from the noise is amplified by the pump beam to get gain. In the teaching here we teach the use of additional seed beam at Raman frequency: one pump photon ($\Omega$) is annihilated (loss) and one strokes photon (Wi) is created (gain). One can achieve large conversion $\geq 1\%$. SRS has no background due to electronic $\chi^3$ (1, 2) as does CARS—four wave mixing.

In the past SRS gain, one used ps and fs lasers in stimulated Raman setup. Combination of ps or fs lasers, cw Rhodamine dyes and He—Ne lasers were used to enhance vibrational modes.

SUMMARY OF THE INVENTION

We teach the use of pairs of continuous diodes for Raman Vibrational Microscope and to modulate diode laser for both the pump and probe beams at different frequencies. The pump laser diode is chopped or modulated and the probe laser diode is detected act as seed beam at modulate frequency. The frequency difference is at the vibrational frequency of the primary, combination mode or overtone modes in brain tissue and neurons, in arteries for plaque and in glucose in blood tree in tissue. In this invention, we teach a method continuous wave weak stimulated Raman gain and loss approach using low power diode lasers in milli-watt range for pumping and probing the key vibrations in materials to map and detect diseases of cancer, plaques, diabetes, heart, Alzheimer, Autism, brain disorder, glucose, eroded plaque and vulnerable plaque inside the body with optical fibers.

The key point of the invention is the use of various pairs of continuous wave modulated diode lasers for SRS microscope source, one as the pump and one as the probe. The difference in frequencies is equal vibrational frequency of molecule of interest. One can alternate the role where in one case SR gain is measured on Stokes and SR loss on AntiStokes role of the pair.

BRIEF DESCRIPTION OF DRAWINGS

The above and other aspects, features and advantages of the present invention will be more apparent from the following description when taken in conjunction with the accompanying drawings, in which:

FIG. 4 (*a*) illustrates Raman signals from cholesterol. Areas 1 and 5—sample excited only at 532 nm, areas 2 and 4—sample excited at 532 nm and 633 nm simultaneously, area 3—sample excited only at 633 nm.

FIG. 4 (*b*) illustrates Raman signals from plaque in artery. Areas 1, 6, and 12—sample excited only at 532 nm, areas 2, 4, 7, 9, and 11—sample excited at 532 nm and 633 nm simultaneously, areas 3 and 8—sample excited only at 633 nm, areas 5 and 10—no excitation. Signal in areas 1, 2, 3, and 4 were measured in one location on the sample, other areas in different 3 locations.

DETAILED DESCRIPTION OF THE INVENTION

Figure 2A:
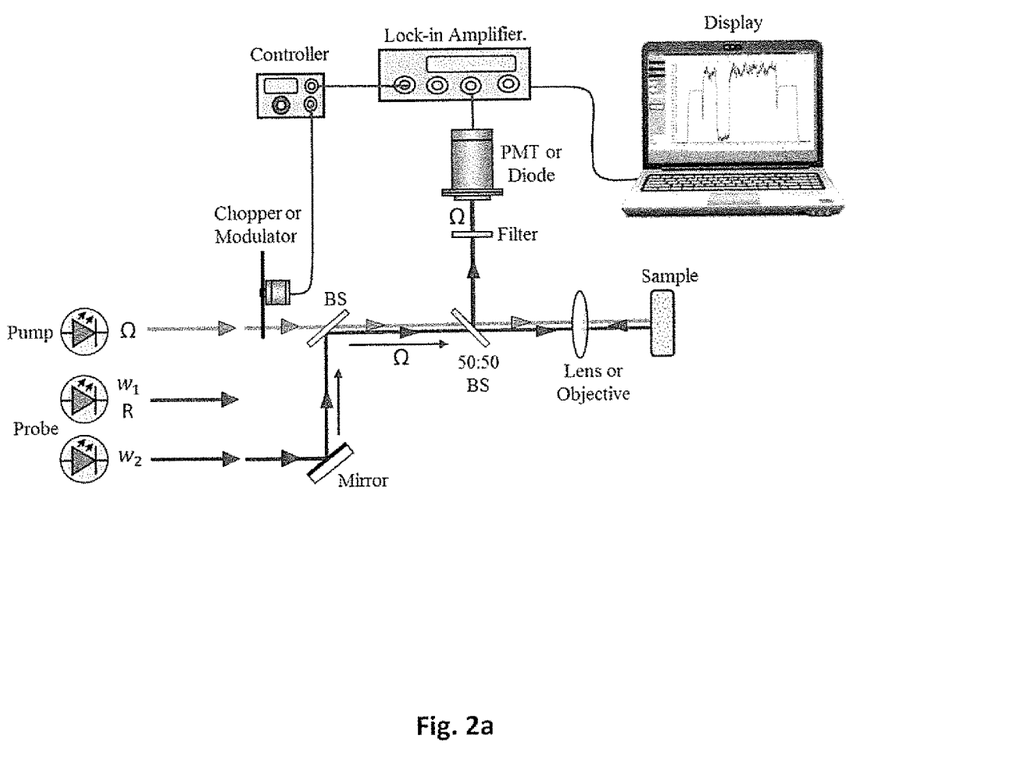
FIG. 2a is a diagrammatic representation of 1D Stimulated Raman Microscope.
Figure 2B:
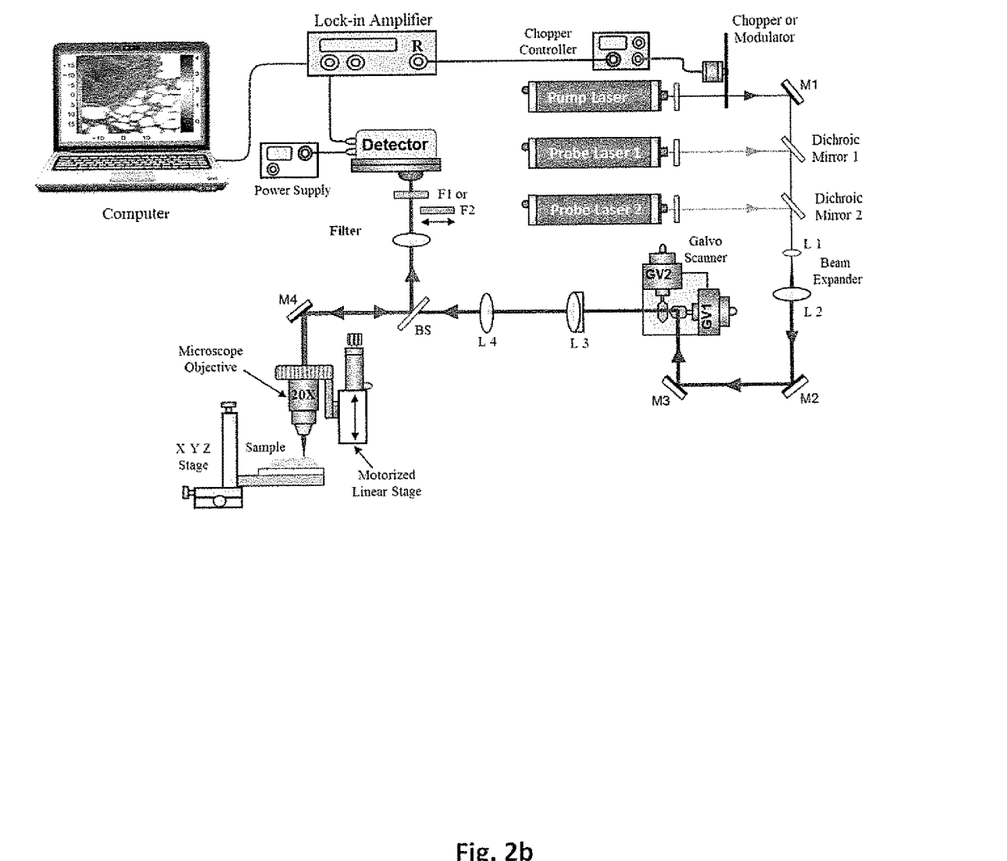
FIG. 2b is a diagrammatic representation of 2D/3D Imaging Stimulated Raman Microscope, where the sample is on a horizontal support.
Figure 2C:
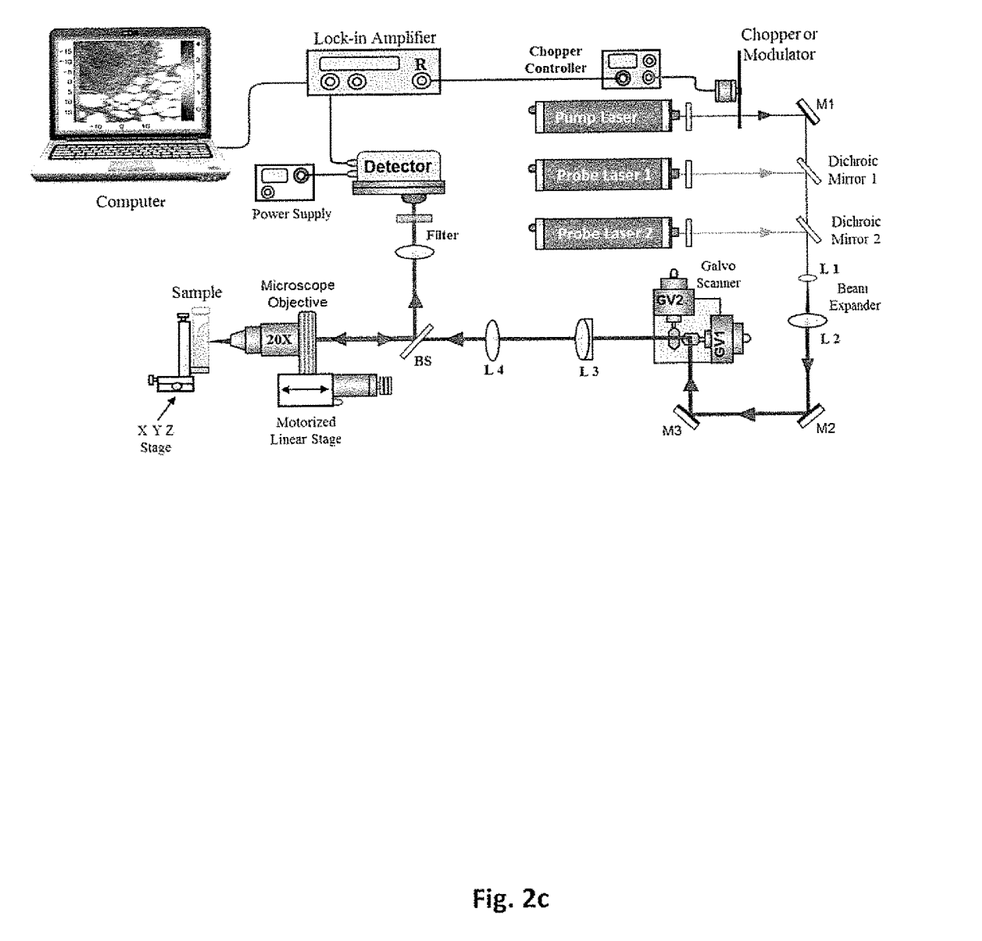
FIG. 2c is a diagrammatic representation of 2D/3D Imaging Stimulated Raman Microscope, where the sample is on a vertical support.

We teach the use of continuous wave diode lasers for a SRS microscope for both pump ($\Omega$) and probe-seed ($W_i$) diode lasers to span many vibration lines $W_Q$. The vibrations excited are: $W_Q = \Omega - W_i$ where $W_Q$ is vibration frequencies of bonds in biomolecule and chemicals in human and animal tissues from cells, cellular parts, nucleus, mitochondrion, ribosomes, DNA, proteins, lipids and extracellular matrix components. Diode lasers are now available for many selective vibration excitations covering wide range of frequencies. These diode lasers can be modulated from 1 Kz to 100 MHz 2D and 3D can be mapped and imaged on a computer by moving the focal spot about the sample say in Z direction (propagation z direction of the diode laser beams by objective lens and the use of pair of mirrors on scanning galvanometer for x and y directions to get 2D and 3D image of the vibrations in the sample. Various designs of SRS gain is shown in FIG. 2a, FIG. 2b and FIG. 2c for 1D, 2D, and 3D Raman plots.

Figure 3:
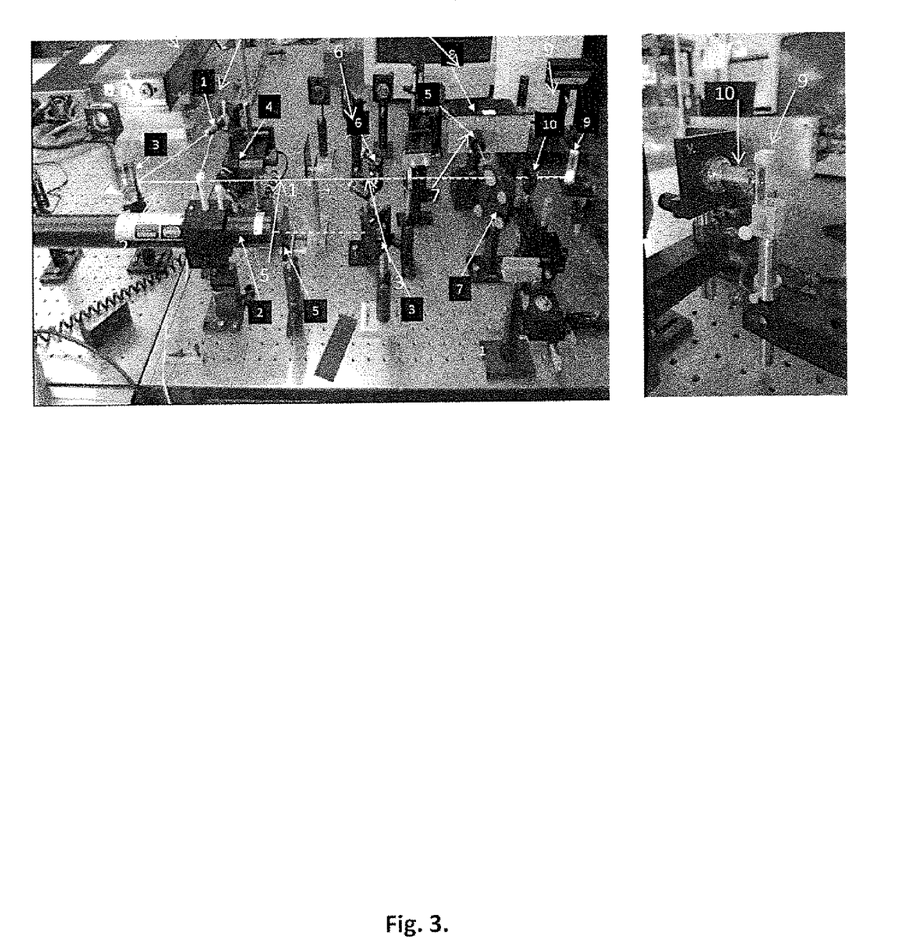
FIG. 3 is a photograph of Stimulated Raman Microscope System and sample with a microscope lens. CW Laser-532 nm 1, HeNe Laser-632 nm 2, Mirror 3, Chopper 4, Filter 5, Dichroic Mirror 6, Beam Splitter 7, Detector 8, Sample 9, Microscope Objective or Lens 10.

The pump diode $\Omega$ and probe diode $W_i$ produce Raman signal due to stimulated driving of Vibrations. For example: cholesterol $W_Q$ frequency of CH bonds is 2891 cm$^{-1}$ (2854 to 2935 cm$^{-1}$) where pump wavelength is $\Omega = 532$ nm and probe wavelength $W_i = 632$ nm. The setup is shown in photos in FIG. 3 with a cholesterol sample.

Figure 4A:
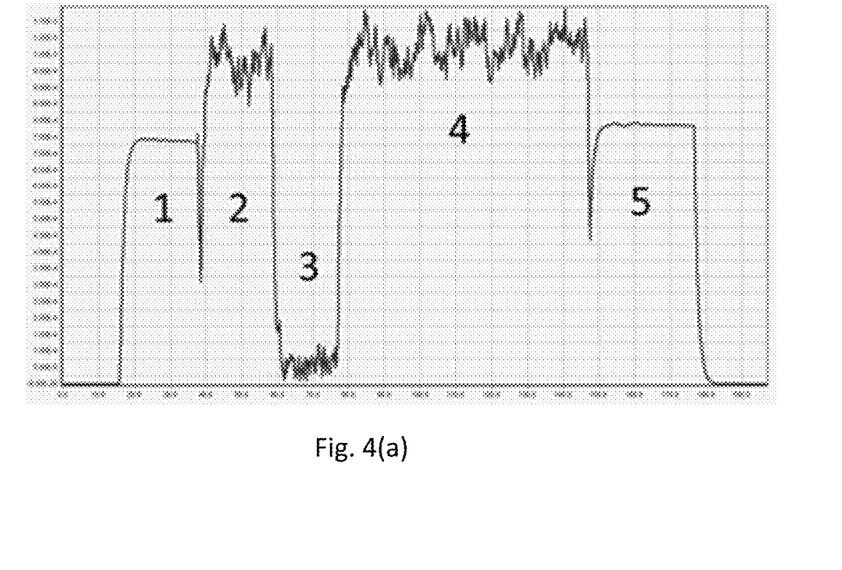
Figure 4B:
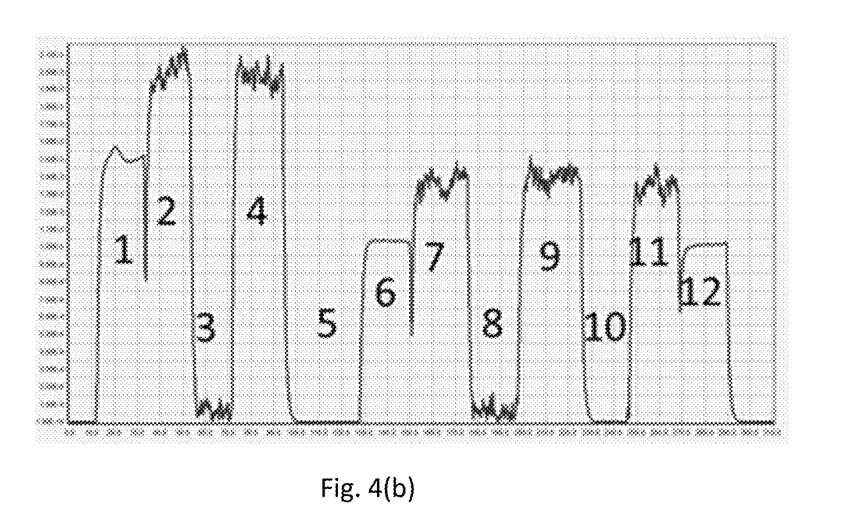

Test results for cw lasers are shown in FIG. 4(*a*) for 532 nm 10 mw diode pump Nd:Yag SHG laser and FIG. 4(*b*) for 5 mw 633 nm He Ne laser for cholesterol. Experimental SRS setup is shown in FIG. 2 and an example is shown in the photo in FIG. 3. These diode lasers $W_i$ can drive the presence of cholesterol, fat, proteoglycans, chondrocytes, LDL, lipids, and HDL molecules(5).

A pair of diode lasers are needed for a vibration, one at $\Omega$ pump and one at $W_i$ probe where $W_Q = \Omega - W_i$ is a vibrational frequency selected to measure the molecules in the sample.

The pump diode laser is chopped or modulated at a frequency, $f_c$, in range from $f_c = 1$ KHz to 100 MHz, say 3 KHz for lock-in detection for a tuned amplifier at $f_c$. Many CW laser diodes are available from Thorlabs Company from 375 nm to 1950 nm with CW powers >20 mW, typically 100 mW.

Several laser diodes can be used in combination, say 532 nm laser diode pump to excite the vibration $W_Q$ to probe with $W_i$ at 632 nm to map these vibration $W_Q$.

The teaching of the patent is shown in FIG. 4, where the signal produced by pump Ω diode lasers and probe diode lasers at $W_i$ is measured in backscatter geometry using a PMT, pin diode, avalanche diode to send signal to lock-in amplifier tuned at chopping frequency, $f_c$. A pair of mirror galvanometer is used to move beam about the sample to obtain a 2D and 3D image of the vibrations in the sample.

Figure 5:
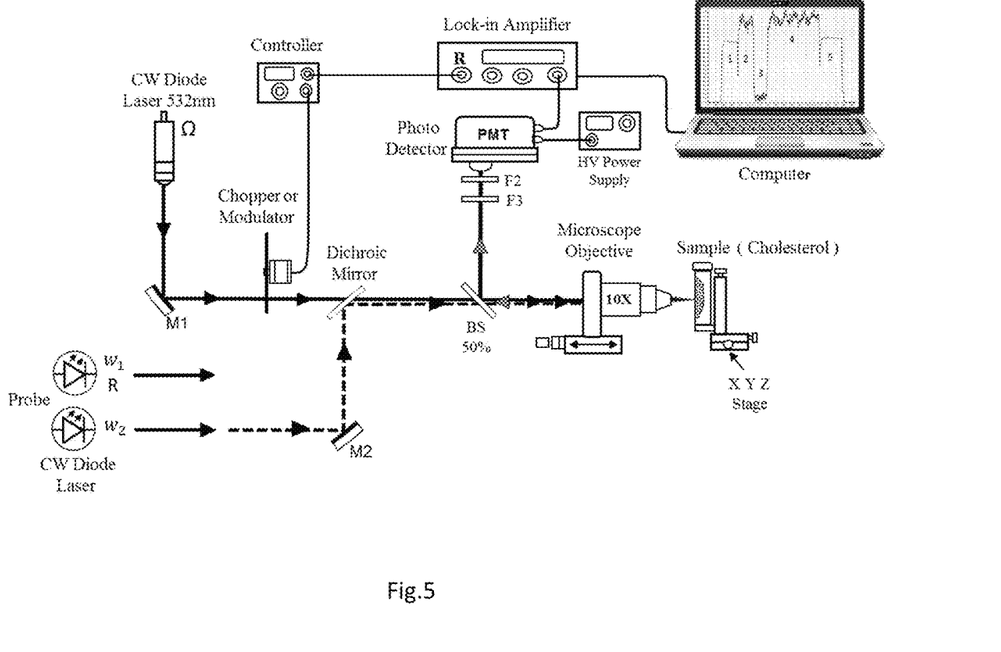
FIG. 5 is a diagrammatic representation of Stimulated Raman CW Diode Laser System.

The stimulated Raman signal $I_{SRG}$ is produced from the diode laser pump $I_L$ at Ω and $I_R$ probe diode laser at $W_i$ is displayed in FIG. 5 computer's screen and stored for analysis. The pump and probe beam on and off and together show the signals for FIG. 4a Cholesterol and FIG. 4b shows the signals for arteries tissue with plaque.

We teach the use of two CW beams a pump at Ω and Raman probe R at $W_i$ causes the stimulated Raman process at $W_i$ are incident into sample. The stimulated Raman signal is produced in back scatter direction gain using a modified De-Beers law—like equation (3,4):

$$I_{SRG}(Wi) = (\sigma I_L + I_R)\text{Exp}(GI_L - \alpha l) \qquad (2)$$

for two laser diode beams. The seeds are spontaneous (first term) and laser probe beam (second term in the bracket) as pre-factor before Exponential. The first term in the bracket is spontaneous Raman ($\sigma I_L$) by diode laser Ω and the second term is probe $I_R$ at $W_i$, G is the Raman gain coefficient, σ is Raman cross section, α is absorption coefficient, and I is interaction distance.

Taking no absorption α=0, the stimulated Raman gain signal at $W_i$ is:

$$I_{SRG}(Wi) = (\sigma I_L + I_R)\text{Exp}(GI_L), \qquad (3)$$

where: $\sigma I_L$ is the spontaneous Raman at $W_i$ for pump laser at Ω, $I_R$ is the seed probe intensity at $W_i$ for CW diode laser at $W_i$. $I_L$ is the intensity if diode pump laser at Ω for small signal gain. $I_{SRG}$ becomes:

$$I_{SRG}(Wi) \approx (\sigma I_L + I_R)(1 + GI_L), \sim \sigma I_L + \sigma GI_L I_L + I_R + GI_L I_R. \qquad (4)$$

For lock-in detection at chopping frequency fc for $I_L$ these Eq 4 reduces to:

$$I_{SRG}(fc)(Wi) = \sigma I_L + GI_L I_R. \qquad (5)$$

Since $I_L$ is modulated only at fc. The change in stimulated Raman signal is given by:

$$\Delta I_{SRG}(Wi) = GI_L I_R. \qquad (6)$$

One can set $I_L \sim I_R$, lower or higher $I_R \sim \frac{1}{10} I_R$ for best S/N gain.

SRS example for cholesterol and artery are shown in FIG. 4 using cw 532 nm laser and HeNe 632 nm laser.

The total detected SRG signed at chopping fc for signal is:

$$I_{SRG}(Wi) \sim \sigma I_L + GI_L I_R \text{ at } f_c. \qquad (7)$$

Example for key vibrations are: CH3 and CH2 and amide types are:
Cholesterol $V_i$=2854 to 2935 cm$^{-1}$, 1440 cm$^{-1}$
Glucose $V_i$=1001 cm$^{-1}$
LDL, HDL, 2850-3000 cm$^{-1}$
Cancer $V_i$=1650 cm$^{-1}$
Artery 2895 cm$^{-1}$

TABLE 1

| Pair CW Diode Lasers and Raman Shifts: | | | | |
|---|---|---|---|---|
| | $\lambda_L$ | $V_L$ | Raman Qi | |
| Ω | 533 nm | 18762 cm$^{-1}$ | | |
| $W_i$ | 632 nm | 15822 | 2940 cm$^{-1}$ | Cholesterol, VP |
| Ω | 632 nm | | | |
| $W_i$ | 690 nm | | 1440 cm$^{-1}$ | Cholesterol, VP |
| Ω | 780 nm | 12838 | | |
| $W_i$ | 880 nm | | 1440 cm$^{-1}$ | Cholesterol, VP |
| Ω | 632 nm | 15822 | | |
| $W_i$ | 690 nm | | 1366 cm$^{-1}$ | Glucose |
| Ω | 632 nm | | | |
| $W_i$ | 680 nm | | 1126 cm$^{-1}$ | Glucose |
| CW Laser Diode Bank Array for SR gain: | | | | |
| 532 nm | Array of diode cw lasers | | | |
| 632 nm | | | | |
| 680 nm | | | | |
| 690 nm | | | | |
| 780 nm | | | | |
| 880 nm | | | | |
| to excite SRS in various molecules in tissue in vivo and ex vivo. | | | | |

While the invention has been shown and described with reference to certain embodiments thereof, it will be understood by those skilled in the art that various changes in form and detail may be made therein without departing from the spirit and scope of the invention as defined by the appended claims and their equivalents.

The invention claimed is:

1. A Raman gain/loss vibrational microscope comprises a continuous wave (cw) pump diode laser for emitting a signal at a pump frequency Ω; at least one generally co-linear probe continuous (cw) diode laser for emitting a Raman signal at a frequency $W_i$, where i≥1; and a chopper or modulator for modulating said pump frequency signal Ω at a frequency $f_c$ where $f_c$ is in the range of 1 KHz to 100 MHz for a lock-in amplifier to detect Raman signal at $W_i$ to generate a stimulated Raman signal by Raman Scattering with a vibrational frequency $W_Q$=Ω-$W_i$ for loss at pump frequency Ω and gain at probe frequency $W_i$.

2. A microscope as defined in claim 1, wherein said CW diode laser signals have an intensity of >1 mw.

3. A microscope as defined in claim 1, wherein said continuous wave (cw) diode lasers are used as a source for a Raman Vibrational Microscope.

4. A method of using a Ramen gain/loss vibrational microscope comprising the steps of generating two separate signal frequencies including a pump frequency Ω using a continuous wave (cw) pump diode laser at a pump frequency Ω and at least one probe frequency using a generally co-linear probe continuous wave (cw) probe diode laser for emitting a signal at a Raman frequency Wi, where i≥1; and modulating said pump frequency signal Ω at a frequency $f_c$ where $f_c$ is in the range of 1 KHz to 100 MHz for a lock-in amplifier to detect Raman signal at $W_i$ to generate a stimulated Raman signal by Raman Scattering; and measuring the Raman signal at $W_i$ with both pump frequency Ω and probe frequency $W_i$ on a sample by a vibrational frequency $W_Q$=Ω-$W_i$ for loss at pump frequency Ω and gain at probe frequency $W_i$.

5. A method as defined in claim 4, wherein said two CW signals at said pump and probe frequencies Ω and $W_i$ are scanned about the sample with a mirror gyro scanner to map vibrational signal SRG post point by point to give 2D and 3D images.

6. A method as defined in claim 4, wherein a SRS signal is used at $W_i$ at Raman frequency for laser pump $\Omega = W_i + W_Q$.

7. A method as defined in claim 4, wherein at least 2 diode laser pairs are used at pump and probe frequencies to obtain selected vibrations including:

| $\Omega$ nm | $W_i$ (nm) | $W_Q$ (cm$^{-1}$) | |
|---|---|---|---|
| 532 nm | 632 nm | 2940 cm$^{-1}$ | FAT/protein |
| 632 nm | 690 nm | 1440 cm$^{-1}$ | FAT |
| 780 nm | 880 | 1440 | FAT |
| 632 nm | 690 | 1336 | Glucose |
| 632 nm | 680 | 1126 | Glucose. |

8. A method as defined in claim 4, wherein a pair of laser diodes are used to detect cancer at $W_Q = 1650$ cm$^{-1}$.

9. A method as defined in claim 4, wherein a pair of laser diodes are used to detect Alzheimer at $W_Q = 2331$ cm$^{-1}$.

10. A method as defined in claim 4, wherein a pair of laser diodes is used to detect plaque at 1440 cm−1 and 2940 cm−1.

11. A method as defined in claim 4, wherein a pair of laser diodes is used to detect cholesterol, LDL, HDL.

12. A method as defined in claim 4, wherein a pair of laser diodes is used to detect proteins, lipids, proteoglycans and chondrocytes from extracellular membrane.

13. A microscope as defined in claim 1, wherein an assembled SRS dual bank of CW diode lasers uses 40×, 20×, 10× objective lenses to focus on a sample.

14. A microscope as defined in claim 1, further comprising optical fibers used to transport said CW laser signals at $\Omega$ and $W_i$ to sample and return a signal at $W_i$.

15. A method as defined in claim 4, wherein the sample comprises at least one of the following animal or human tissues or cells: brain, cervix, colon, artery, oral, stomach and bladder.

16. A method as defined in claim 4, further comprising 2D and 3D vibration $W_i$ images of tissue by moving the sample and/or a galvanometer.

17. A method as defined in claim 4, wherein $W_Q$ corresponds to a vibration of one of blood chemical constituents analytes including glucose, cholesterol, lipids, fat, proteoglycans, chondrocytes, LDL and HDL molecules.

18. A method as defined in claim 1, wherein two generally co-linear probe continuous (cw) diode lasers are provided for emitting Raman signals.

19. A method as defined in claim 18, wherein said continuous wave (cw) pump diode laser is arranged to emit a signal at said pump frequency in a direction generally perpendicular to a direction corresponding to a direction of said generally co-linear Raman signal of said at least one probe laser; and beam direction modifying means for orienting all emitted beams in a substantially co-linear direction to direct said beams onto a sample to be analyzed.

* * * * *